United States Patent [19]

Svoboda et al.

[11] 4,017,261

[45] Apr. 12, 1977

[54] BIOLOGICAL DIAGNOSTIC TEST STRIP AND METHOD OF PRODUCING SAME

[75] Inventors: Vlastimil Svoboda; Olga Celchovska, both of Brno, Czechoslovakia

[73] Assignee: Lachema, narodni podnik, Brno, Czechoslovakia

[22] Filed: Oct. 16, 1975

[21] Appl. No.: 622,833

[30] Foreign Application Priority Data

Oct. 16, 1974 Czechoslovakia ............... 7070/74

[52] U.S. Cl. .................... 23/253 TP; 23/230 B; 195/103.5 R; 252/408

[51] Int. Cl.² ............... G01N 21/06; G01N 31/22; G01N 33/16

[58] Field of Search ............... 23/230 B, 253 TP; 195/103.5 R; 252/408

[56] References Cited

UNITED STATES PATENTS

| | | | |
|---|---|---|---|
| 3,252,762 | 5/1966 | Adams | 23/253 TP |
| 3,290,117 | 12/1966 | Adams | 23/253 TP |
| 3,411,887 | 11/1968 | Ku | 23/253 TP |
| 3,418,083 | 12/1968 | Rey | 23/253 TP |
| 3,453,180 | 7/1969 | Fraser | 23/253 TP X |
| 3,627,697 | 12/1971 | Rey | 23/253 TP X |
| 3,627,698 | 12/1971 | Rey | 23/253 TP X |
| 3,654,179 | 4/1972 | Bauer | 23/253 TP X |
| 3,668,076 | 6/1972 | Rey | 23/253 TP X |
| R28,575 | 10/1975 | Bauer | 23/253 TP X |

OTHER PUBLICATIONS

Chemical Abstracts, 80:142768g and 14769h (1974).

*Primary Examiner*—Joseph Scovronek
*Assistant Examiner*—Sidney Marantz

[57] ABSTRACT

Diagnostic test strips for the qualitative detection and semi-quantitative estimation of blood and hemoglobin in biological products include a reagent area comprising an acid buffer having a pH within the range of 2.5–5.0, a chromogen, a wetting agent, an agent capable of enhancing the peroxidase activity of hemoglobin, an organic hydroperoxide in the form of a stable, solid salt with an aliphatic, alicyclic or heterocyclic amine, and a solid, polymeric film forming material disposed upon an adsorbent bibulous carrier.

7 Claims, No Drawings

BIOLOGICAL DIAGNOSTIC TEST STRIP AND METHOD OF PRODUCING SAME

This invention relates to diagnostic test strips. More particularly, the present invention relates to diagnostic test strips suitable for the qualitative detection and semi-quantitative estimation of blood and hemoglobin in biological products.

The occurrence of blood or hemoglobin in urine and feces, the so-called hematuria, hemoglobinuria or occult bleeding, is symptomatic of certain severe disorders, the early diagnosis of which is significant from the standpoint of efficient therapeutic treatment. Thus, for example, hematuria, the presence of blood or erythrocytes in urine, is commonly associated with numerous nephropathies, such as uremia, acute or chronic exacerbated nephritis, acute tubular nephrosis, pyelonephritis, nephrolithiasis or tuberculosis of the urogenital system, congenital polycystic kidneys and the like. It may also be associated with certain circulation disorders such as hemorrhagic infarction of the kidney, kidney congestion in cardiac insufficiency, thrombosis of renal veins, overdosage of anti-coagulant drugs and the like. Hemoglobinuria, on the other hand, occurs in certain hemolytic diseases or disorders such as hemolytic anemia, poisoning due to bacterial or fungal toxins or chemicals, nocturnal hemolysis due to the lysins, crush syndrome, hemolytical nephrosis after transfusions of incompatible blood and the like.

Occult bleeding into the stool is symptomatic of disorders of the gastro-intestinal tract such as stomach polyposis, ulcerous diseases, gastric, duodenal or intestinal carcinoma, ulcerative inflammation of the colon and the like.

Heretofore, the rapid detection and semi-quantitative estimation of erythrocytes and hemoglobin in biological materials such as urine has been effected by the use of diagnostic test strips which take advantage of the peroxidase activity of hemoglobin. The strips employed for this purpose include a test area which contains an organic hydroperoxide such as phenylisopropyl hydroperoxide, phenyl-1,4-diisopropyl dihydroperoxide, 1-hydroxycyclohexane-1-hydroperoxide, tertiary butyl hydroperoxide and the like. Additionally, there is included in the test area an acid buffer having a pH within the range of 4–7, a colorless chromogen capable of being oxidized to a colored product such as o-tolidine, benzidine, 2,7-diaminofluorene, guaiacol, substituted phenylene diamines of the type described in U.S. Pat. No. 3,092,464, such as o-dianisidine, pyridine derivatives of the type described in British Pat. No. 1,182,898 or substituted azines of the type described in British Pat. No. 1,186,668.

The diagnostic test strips as described are immersed in erythrocytes, or free hemoglobin containing urine, which results in oxidation of chromogen by hydroperoxide and in conversion thereof to an intensely colored product by catalytic peroxidase action of hemoglobin, the intensity and speed of color formation being proportional to the amount of hemoglobin present.

Although the oxidation of chromogens is accelerated by the catalytic action of hemoglobin and related compounds with peroxidase activity, studies have revealed that such oxidation occurs even without catalysis. Accordingly, the principal components of the test area of the diagnostic strips, namely the hydroperoxide and the chromogen, must be segregated from each other to avoid premature discoloration and deterioration. Furthermore, exposure of the strips to ambient humidity during storage enhances the speed of spontaneous chromogen oxidation and the innate volatility of the hydroperoxides often causes a loss in reactivity during storage.

These limitations have heretofore been obviated by encapsulation of microdroplets of hydroperoxide within microscopic celluloid bubbles, so precluding both volatilazation thereof and chromogen contact. Unfortunately, this approach is complex and the strips so prepared evidence low hemoglobin sensitivity and a slow rate of reaction since the microcapsules must swell and rupture upon contact with the liquid being analyzed before liberation of hydroperoxide. Furthermore, it has been found that this process is not uniform for all liquid or urine specimens so that the volume of liberated hydroperoxide is unpredictable. A further limitation arises from spontaneous hardening of microcapsule shells during lengthy storage, so resulting in reaction of the strips after a time delay only with a limited sensitivity. Thus, for example, strips of this type evidence a positive reaction with erythrocytes or hemoglobin only if the latter are present in an amount exceeding from 50,000 to 100,000 erythrocytes per 1 ml. of urine, a sensitivity which does not meet the requirements of clinical chemistry since it is an order of magnitude less than that required for diagnostic purposes. Physiological hematuria is characterized by the excretion of blood in an amount on the order of 3,000 erythrocytes per 1 ml. of urine and 5,000 erythorcytes per 1 ml. of urine is regarded as pathological.

In accordance with the present invention, the foregoing prior art limitations are successfully obviated by the use of a novel diagnostic test strip wherein the test or reagent area of the strip includes an acid buffer having a pH within the range of 2.5–5.0, a chromogen, a wetting agent, an agent capable of enhancing the peroxidase activity of hemoglobin, an organic hydroperoxide in the form of a stable, solid salt with an aliphatic, alicyclic or heterocyclic amine, and a solid, polymeric film-forming material or synthetic substance, the reagents being disposed upon an adsorbent bibulous carrier material.

The organic hydroperoxides suitable for use in the practice of the present invention may conveniently be selected from among tertiary butyl hydroperoxide, phenylisopropylhydroxide, 4-methylphenylisopropyl hydroperoxide, phenyl-1, 4-diisopropyl dihydroperoxide, 1-hydroxycyclohexyl-1-hydroperoxide, and 2,5-dimethylhexane-2,5-dihydroperoxide. As indicated above, the hydroperoxide is employed in the form of a stable, solid non-volatile salt with an aliphatic, alicyclic or heterocyclic amine. The amines found suitable for the purpose must evidence a pK of at least 8.0 and may be selected from among piperazine, (1, 4, diazabicyclo-2,2,2-octane) octane, urea, hexamethylene tetramine, 2-amino-2-methyl-1, 3-propandiol, 3,3'-diamino-2-propanol, 3,3'-diaminodipropylamine, mono and diethanolamine and cyclohexylamine. These salts are prepared by reacting the amine with the hydroperoxide as described by A. A. Oswald et al in Journal of Organic Chemistry, Volume 26, page 3969, 1961. However, the use of such salts in diagnostic strips of the type described herein has not previously been reported in the literature.

The salts of organic hydroperoxides are preferably used in a mixture with a 0.1 to 10 molar excess of the amine which stabilizes the hydroperoxide salt. It will be appreciated by those skilled in the art that any of the aforementioned amines may be used in combination with any salt, a solid nonhygroscopic water soluble salt being considered an advantageous element in the test strip.

The crystalline organic amine salts are typically employed herein in a non-aqueous solvent such as benzene, toluene, diethyl ether, choroform, ethylenedichloride, petroleum ether, ethyl acetate and the like. A general preference exists for a combination of the foregoing solvents with a $C_1 - C_3$ alkanol.

As indicated, the test area of the diagnostic strip also includes a polymeric, natural or synthetic filmforming organic substance which is capable of protecting the test area against the deleterious influence of ambient humidity and air and precluding premature contact of reagents during the preparative process. The organic substance employed must be water soluble, soluble in the described non-aqueous solvents, incapable of participating in the oxidation reaction and following evaporation of the solvent must be capable of forming a partially water wettable film on the bibulous carrier. Materials meeting these requirements are sodium alginate, polyvinylpyrrolidone, polyvinyl alcohol, starch, polyvinyl propionate, polyvinyl butyral, carboxymethyl cellulose, polyethylene glycols having a molecular weight within the range of 2,000–15,000 or mixtures of any of the foregoing.

Other components of the test area may be selected from among any of the well-known prior art materials employed for such purposes. Thus, buffers comprising a mixture of a polyvalent organic or inorganic acid having a pK ranging from 1.0–5.0, sodium, potassium or ammonium salts thereof or mixtures of primary or secondary salts of such acids may be used. Typical of such buffers are mixtures of citric acid and sodium citrate, tartaric acid and sodium tartrate, malic acid and borax, potassium hydrogen phthalate and dipotassium phthalate, sodium hydrogen succinate and disodium succinate, and the like. The specific buffer chosen and the concentration thereof is not critical, the prime requirement being the maintenance of a pH in the test area upon immersion in the liquid to be tested in the range of 2.5–5.0.

The wetting agent employed is designed to enhance the absorptivity of the test area and hence the reaction rate. For this purpose any of the well-known anionic, nonionic or cationic detergents may be employed. A general preference has been found to exist for anionic detergents which are found to provide superior sensitivity.

Optionally, there may be included in the reagent combination an agent capable of enhancing the peroxidase activity of hemoglobin. Agents satisfying this requirement may be selected from among quinoline and its derivatives such as quinine, cinchonine, 6-methoxyquinoline, quinaldine, 8-amino-6-methoxy-quinoline, 2-quinolinol and the like as described in British Pat. No. 1,057,056. As noted, the presence of such reagents accelerates the rate of the oxidation reaction and enhances the color intensity of the oxidized chromogen which yields higher sensitivity.

The critical feature of the present invention resides in proper segregation of the acid buffer and chromogen from the organic peroxide salt and the organic amine. this end is attained by impregnating an adsorbent carrier, such as filter paper, with an aqueous or aqueous alcoholic solution of the buffer and chromogen and, subsequently, after thorough drying the resultant impregnated layer is overlaid with the solution of organic hydroperoxide salt and an excess of amine. This second solution is prepared in the non-aqueous solvent described above. The other components of the test area may be included in either of the two impregnation solutions. The specific order of addition is not critical although in certain instances it may be advantageous to employ one material in the first impregnation step. Thus, for example, the use of anionic lauryl sulfate or sodium dioctylsulfosuccinate as a wetting agent in the first impregnation step and polyvinyl alcohol as the organic film-forming substance are advantageous whereas the use of non-ionic polyoxyethylene lauryl ether or ethoxylated oleyl alcohol polyvinyl pyrrolidone as the film-forming material are advantageously used in the second impregnation step. It is also feasible to prepare the described diagnostic strips in a three step impregnation process wherein the first impregnation includes the buffer, chromogen, peroxidase activity potentiating agent anionic detergent and filmforming substance, the second impregnant including polyvinyl alcohol or sodium alginate and wetting agent and the third impregnant including the organic hydroperoxide salt, the organic amine, non-ionic detergent and organic film-forming substance. Thorough drying of the paper being impregnated is, of course, required prior to each impregnation.

When ready for use, diagnostic strips prepared in the foregoing manner are immersed in an aqueous liquid such as urine, the components of the test area coming into contact with each other. Under contact conditions, the reactive hydroperoxide is freed from its salt by the action of the acid buffer and the former oxidizes in the presence of hemoglobin and converts the chromogen to a colored product.

The virgin strips prior to use are a pale cream yellow color and upon immersion in a liquid free of blood or hemoglobin retain this color. However, in the presence of blood or hemoglobin in minute quantities they turn an intensive bright blue, the intensity being directly proportional to the amount of blood or hemoglobin in the liquid being tested. Comparison of the colored test area with a standard color chart permits a semi-quantitative evalutation with a high degree of accuracy.

Studies have revealed that test strips prepared in accordance with the present invention evidence a bright blue coloration in the presence of from 1-2 erythrocytes in 1 ml. of water and from 5–10 erythrocytes in 1 ml. of urine, the lowest pathological amounts of blood or hemoglobin in urine. This degree of sensitivity has not heretofore been achieved by similar test procedures and compares favorably with the well-known microscopic methods.

In order to preclude deterioration prior to use, it has been found useful to store the described test strips in closed containers in the presence of a dessicant such as silica or a molecular sieve.

Several examples of the present invention are set forth below. It will be appreciated by those skilled in the art that these examples are set forth merely for purposes of exposition and are not to be construed as limiting.

EXAMPLE 1

A first solution was prepared by dissolving 5 grams of O-tolidine hydrochloride in a mixture comprising 100 ml. of a 5% aqueous polyvinylpyrrolidone solution and 150 ml. of ethyl alcohol. 150 ml. of 2N citrate buffer having a pH of 3.7 were then added to the resultant solution followed by 50 ml. of a 10% aqueous lepidine hydrochloride solution and 10 ml. of a 5% solution of sodium lauryl sulfate in water.

A second solution was then prepared by dissolving 40 grams of 1,4-diazabicyclo-2,2,2-octane salt of phenyiisopropyl hydroperoxide, 50 grams of 1,4-diazabicyclo-2,2,2-octane and 20 grams of solid polyvinylpyrrolidone in 1,000 ml. of a 4 percent solution of polyvinylpyrrolidone in a 2:1 mixture of toluene and ethyl alcohol.

The carrier chosen for impregnation was a 150 g/m² thick sheet of filter paper having a width of 80 mm and a hydrophobic barrier 6 mm from one longitudinal edge thereof, the barrier being formed by impregnation of the paper with a 5 percent solution of ethyl cellulose in ethyl alcohol followed by drying.

The carrier was initially impregnated with the first solution, described above, by adding 2.0 ml. of the solution per meter of carrier between the edge of the sheet and the barrier. The impregnated sheet was then dried in hot air at a temperature within the range of 80–85° C.

Following, a second impregnation was effected by adding 1.5 ml of second solution per meter of sheet and drying in the previous manner. The resultant sheet was then cut, in the transverse direction, into 6 mm wide strips from which 6 mm wide diagnostic strips having a length of 80 mm were obtained. The test area of such strips was approximately 6 × 6 mm. and was separated from the remainder thereof by the hydrophobic barrier. The color of the test area was pale cream and retained such coloration until immersed in a solution containing blood or hemoglobin. Under such circumstances, the color of the strip turned an intense blue. The first evidence of blue coloration was found to occur with a dilution of 1 part blood in 5 million parts of water and 1 part blood in 1 million parts of urine which corresponds with approximately 4-6 erythrocytes in 1 microliter of urine.

EXAMPLE 2

A first solution was prepared by adding successively to a solution of 5 grams of o-tolidine hydrochloride in 125 ml. of water 125 ml. of a 5% aqueous solution of polyvinylpyrrolidone, 100 ml. of a citrate buffer having a pH of 3.0, 50 ml. of a 10% solution of 2,4-dimethylquinoline hydrochloride in water and 30 ml. of a 5% polyoxyethylene laurylether solution in alcohol.

A second solution was prepared by dissolving 20 grams of the salt of phenylisopropyl hydroperoxide with 1, 4-diazabicyclo-2,2,2-octane and 25 grams of piperazine in 500 ml. of a 4% solution of polyvinylpyrrolidone in a 1:2 mixture of ethanol and benzene.

Diagnostic strips were then prepared in accordance with the procedure set forth in Example 1. The properties of the strips so prepared were similar to those of Example 1.

EXAMPLE 3

A first solution was prepared by adding successively to a solution of 5.0 grams of 2,7-diaminofluorene hydrochloride in 250 ml of a 2% aqueous polyvinylpyrrolidone solution, 150 ml. of 2N citrate buffer having a pH of 4.0, 40 ml. of a 10% aqueous solution of quinoline hydrochloride and 1 ml. of isooctylphenoxyethoxyethanol-ethyleneoxide copolymer.

A second solution was prepared by dissolving 25.6 grams of 1-hydroxycyclohexyl-1-hydroperoxide and 60.7 grams of 1,4-diazobicyclo-2,2,2-octane in 1,000 ml of a 4% solution of polyvinyl pyrrolidone in a 1:2 ethanol-chloroform mixture. The solution was permitted to stand in a tightly closed flask in a dark place for 48 hours prior to use.

Impregnation of a carrier was then effected in accordance with the procedure of Example 1. The resultant strips reacted with blood in water having a dilution of 1:2.5 million parts and with blood in urine at a dilution of 1:500,000 parts.

EXAMPLE 4

A first solution was prepared by mixing 200 ml. of 2N citrate buffer having a pH of 3.7 with 200 ml. of a 2.5% aqueous polyvinylpyrrolidone solution and 60 ml. of a saturated solution of o-tolidine hydrochloride in 40% ethanol. Subsequently, 20 ml. of a 10% aqueous lepidine hydrochloride solution and 40 ml. of a 5% solution of sodium dioctylsulfosuccinate in ethanol were added.

A second solution was prepared by dissolving 10 grams of phenyliospropyl hydroperoxide and 40 grams of 2-amino-2-methyl-1,3-propanediol in 500 ml. of a 5% solution of polyvinylpyrrolidone in a 3:1 toluene-ethanol mixture and 10 ml. of a 5% alcohol polyoxyethylene-laurylether solution. The resultant solution was permitted to stand for 48 hours prior to use.

Diagnostic strips manifesting properties similar to those of Example 1 were then prepared in accordance with the procedure therein described.

EXAMPLE 5

A first solution was prepared by dissolving 10 grams of o-tolidine hydrochloride in a mixture of 200 ml of a 5% aqueous polyvinylpyrrolidone solution and 300 ml. of ethanol. 100 ml. of a 10% aqueous lepidine hydrochloride solution, 100 ml. of 2N citrate buffer having a pH of 3.7 and 10 ml. of a 5% aqueous solution of sodium lauryl sulfate were then added.

A second solution was prepared by mixing a 1.25% aqueous solution of polyvinyl alcohol with 20 ml of a 5% aqueous solution of sodium laurylsulfate.

A third solution was prepared by dissolving 40 grams of the salt of phenylisopropyl hydroperoxide with 1,4-diazabicyclo-2,2,2-octane, 60 grams of 1,4-diazabicyclo-2,2,2-octane and 20 grams of solid polyvinylpyrrolidone in 1,000 ml. of a 4% solution of polyvinylpyrrolidone in a 2:1 toluene-ethanol mixture.

Diagnostic strips were then prepared in the manner set forth in Example 1 with similar results being obtained.

What is claimed is:

1. Diagnostic test strip for the detection and semiquantitative estimation of blood and hemoglobin in biological materials comprising a bibulous carrier impregnated with a composition of matter comprising (a) an acid buffer having a pH within the range of 2.5–5.0, (b) a chromogen, (c) an agent capable of enhancing the peroxidase activity of hemoglobin, (d) a wetting agent, (e) a solid, polymeric film-forming substance, and (f) an amine salt of an organic hydroperoxide.

2. Diagnostic test strip in accordance with claim 1, wherein the hydroperoxide salt comprises the reaction product of an organic hydroperoxide with an amine selected from the group consisting of aliphatic, alicyclic and heterocyclic amines having a pK of at least 8.0, said hydroperoxide being selected from the group consisting of tertiary butyl hydroperoxide, phenylisopropyl hydroperoxide, 4-methylphenylisopropyl hydroperoxide, phenyl-1, 4-diisopropyl-dihydroperoxide, 1-hydroxycyclohexyl-1-hydroperoxide, and 2,5-dimethylhexane-2,5-dihydroperoxide.

3. Diagnostic test strip in accordance with claim 1, wherein the bibulous carrier is filter paper.

4. Diagnostic test strip in accordance with claim 1, wherein the o-dianisidine chromogen is selected from the group consisting of benzidine, o-tolidine, guaiacol and 2,7-diaminofluorene.

5. Diagnostic test strip in accordance with claim 1, wherein the wetting agent is selected from the group consisting of anionic, non-ionic and cationic detergents.

6. Diagnostic test strip in accordance with claim 1, wherein the film-forming substance is selected from the group consisting of starch, polyvinyl alcohol, polyvinylpropionate, polyvinyl butyral, carboxymethylcellulose, polyvinyl pyrrolidone and polyethylene glycol.

7. Method for the preparation of a diagnostic test strip for the detection and semi-quantitative estimation of blood and hemoglobin in biological materials which comprises the steps of
  a. impregnating an adsorbent carrier with a solution of an acid buffer having a pH within the range of 2.5–5.0, and a chromogen,
  b. drying the resultant impregnated material at elevated temperatures,
  c. impregnating the dried carrier with a hydroperoxide salt comprising the reaction product of an organic hydroperoxide with an amine selected from the group consisting of aliphatic, alicyclic and heterocyclic amines having a pK of at least 8.0, and
  d. drying the resultant impregnated carrier.

* * * * *